(12) United States Patent
Kanno et al.

(10) Patent No.: US 6,392,094 B2
(45) Date of Patent: May 21, 2002

(54) METHOD FOR RECOVERING AMINO ACIDS

(75) Inventors: Takashi Kanno; Koji Sayama; Tsutomu Aritsuka; Hiroto Kikuchi, all of Hokkaido (JP)

(73) Assignee: Nippon Beet Sugar Mfg. Co., Ltd., Tokyo (JP)

( * ) Notice: Subject to any disclaimer, the term of this patent is extended or adjusted under 35 U.S.C. 154(b) by 0 days.

(21) Appl. No.: 09/883,218

(22) Filed: Jun. 19, 2001

(30) Foreign Application Priority Data

Jun. 21, 2000 (JP) ........................ 2000-226111
Jun. 30, 2000 (JP) ........................ 2000-237745

(51) Int. Cl.[7] ..................... C07C 227/00; C07C 229/00; B01D 15/04
(52) U.S. Cl. ....................... 562/554; 562/554; 562/562; 562/573; 210/692; 210/660
(58) Field of Search ................... 210/692, 660, 210/674, 675, 676; 127/46.2; 562/554, 562, 573

(56) References Cited

U.S. PATENT DOCUMENTS 5,198,120 A * 3/1993 Masuda et al.
6,099,654 A * 8/2000 Kaneko et al.

FOREIGN PATENT DOCUMENTS

| FR | 1248113 | * 10/1959 |
| FR | 1195655 | * 11/1959 |
| JP | 2000-109453 | * 4/2000 |

* cited by examiner

Primary Examiner—Gary Geist
Assistant Examiner—Farhad Forohar
(74) Attorney, Agent, or Firm—Sughrue Mion, PLLC

(57) ABSTRACT

A method for recovering amino acids, which comprises supplying a mixed solution containing inorganic acid salts, amino acids and non-electrolytes such as saccharides to a first-step resin layer comprising an Na type or K type strongly acidic ion exchange resin; separating an effluent into at least a first fraction containing coloring matters, acidic amino acids and ashes, a second fraction containing neutral amino acids and saccharides, and a third fraction containing betaines; supplying the second fraction to a second-step resin layer comprising at least one resin selected from the group consisting of $NH_4$ type, Ca type and Mg type strongly acidic ion exchange resins, and optionally further supplying it to a third-step resin layer comprising an Mg type or Ca type strongly acidic ion exchange resin different from the resin of the second-step resin layer, thereby recovering various kinds of amino acids contained in an effluent.

14 Claims, 12 Drawing Sheets

○;saccharides    ●;ashes and amino acids

METHOD FOR RECOVERING AMINO ACIDS

FIELD OF THE INVENTION

The present invention relates to a method for recovering various kinds of amino acids from a mixed solution comprising inorganic acid salts, coloring matters, ashes, betaines, amino acids and non-electrolytes such as saccharides. In the course of producing sucrose from sugar beets, impurities other than sucrose move into molasses. The molasses still contains sucrose in about a half amount, so that sucrose has further been recovered from the molasses by ion chromatography (hereinafter also referred to as "CR"). Residues containing sucrose which can not be recovered and trace amounts of amino acids have been treated as "CR waste liquor". Further, in the production of sucrose, when ion exchange resins used for purification of sugar liquid in the process of sugar manufacture are regenerated, trace amounts of amino acids adsorbed by the ion exchange resins are eliminated together with regenerating solutions to flow out. This effluent liquor has also been treated as "resin waste liquor". These CR waste liquor and resin waste liquor have hitherto been subjected to the activated sludge process and discarded, or only condensed for utilization as organic fertilizer. The present invention relates to a novel method for recovering amino acids, which makes it possible to recover trace amounts of amino acids existing in such waste liquor.

BACKGROUND OF THE INVENTION

Previously, CR has been utilized as one method for separating respective ingredients from solutions containing the multiple ingredients, such as natural material solutions. However, it has been practically impossible to industrially utilize CR as such for separating trace amounts of ingredients, considering the price of products obtained. Because it necessitates large-scale equipment and a large amount of treating liquid. Many processes have been therefore contrived for industrially using CR. For example, the present inventors have disclosed in Japanese Patent Publication No. 56-39640 that only fractions having sucrose/raffinose ratios within a specific range are collected by separation through a salt type strongly acidic ion exchange resin, and fractionally crystallized, which makes it possible to industrially produce raffinose from sugar beet molasses. Further, as to a method for separating materials similar to those in the present invention, one invention is disclosed in Japanese Patent Laid-Open Publication (Hei) 6-276995. This invention is directed to a method for producing a raw flavoring material, which comprises supplying CR waste liquor or resin waste liquor to a sodium type strongly acidic ion exchange resin to allow amino acids to be adsorbed thereby, and then, eluting them with a solution of sodium hydroxide through a hydrogen ion type weakly acidic ion exchange resin connected to the back of the sodium type strongly acidic ion exchange resin.

The object of the invention described in Japanese Patent Laid-Open Publication (Hei) 6-276995 is to obtain an amino acid-rich fraction, and the fraction can be used as a raw flavoring material. However, the fraction contains materials other than amino acids, and this invention is not directed to a method for recovering only amino acids.

SUMMARY OF THE INVENTION

An object of the present invention is to provide a method for recovering various kinds of amino acids from a solution containing trace amounts of amino acids in a highly concentrated inorganic acid salt or a highly concentrated non-electrolyte such as saccharide, for example, CR waste liquor or resin waste liquor.

The present invention relates to a method for recovering amino acids, which comprises (1) supplying a mixed solution containing inorganic acid salts, coloring matters, ashes, betaines, amino acids and non-electrolytes such as saccharides to a first-step first resin layer comprising a sodium type strongly acidic ion exchange resin (hereinafter also referred to as an "Na type IER") or a potassium type strongly acidic ion exchange resin (hereinafter also referred to as a "K type IER"), (2) separating an effluent which flows out of the first resin layer using water or an aqueous solution of a caustic alkali as an eluent into at least a first fraction containing coloring matters, acidic amino acids and ashes, a second fraction containing neutral amino acids and saccharides, and a third fraction containing betaines, (3) supplying the second fraction to a second-step resin layer comprising at least one resin selected from the group consisting of an ammonium type strongly acidic ion exchange resin (hereinafter also referred to as an "$NH_4$ type IER"), a calcium type strongly acidic ion exchange resin (hereinafter also referred to as a Ca type IER") and a magnesium type strongly acidic ion exchange resin (hereinafter also referred to as an Mg type IER"), and (4) recovering various kinds of amino acids contained in an effluent which flows out of the second-step resin layer.

In the present invention, the term "neutral amino acids" means neutral amino acids including neutral aromatic amino acids such as tyrosine, in a broad sense.

Also, in the present invention, the term "a caustic alkali" means alkali hydroxide including sodium hydroxide and potassium hydroxide.

As to an eluent used for the ion exchange resin in the present invention, an aqueous solution of ammonia is used for the $NH_4$ type IER, water or an aqueous solution of a caustic alkali for the Na type or K type IER, and water for the Ca type IER and the Mg type IER.

Further, when the above-mentioned second-step resin layer is the Ca type IER, the effluent which flows out of the second-step resin layer may be further partly supplied to a third-step resin layer comprising the Mg type IER to recover various kinds of amino acids contained in an effluent which flows out of the third-step resin layer using water as an eluent (which means "recovering method 2-2-A" described later).

Furthermore, when the above-mentioned second-step resin layer is the Mg type IER, the effluent which flows out of the second-step resin layer may be further partially supplied to a third-step resin layer comprising the Ca type IER to recover various kinds of amino acids contained in an effluent which flows out of the third-step resin layer using water as an eluent (which means "recovering method 3-2-A" described later).

As the eluent for the above-mentioned first resin layer, there may be used an aqueous solution of a caustic alkali having a pH of 8.5 to 11.0.

Figure 1:
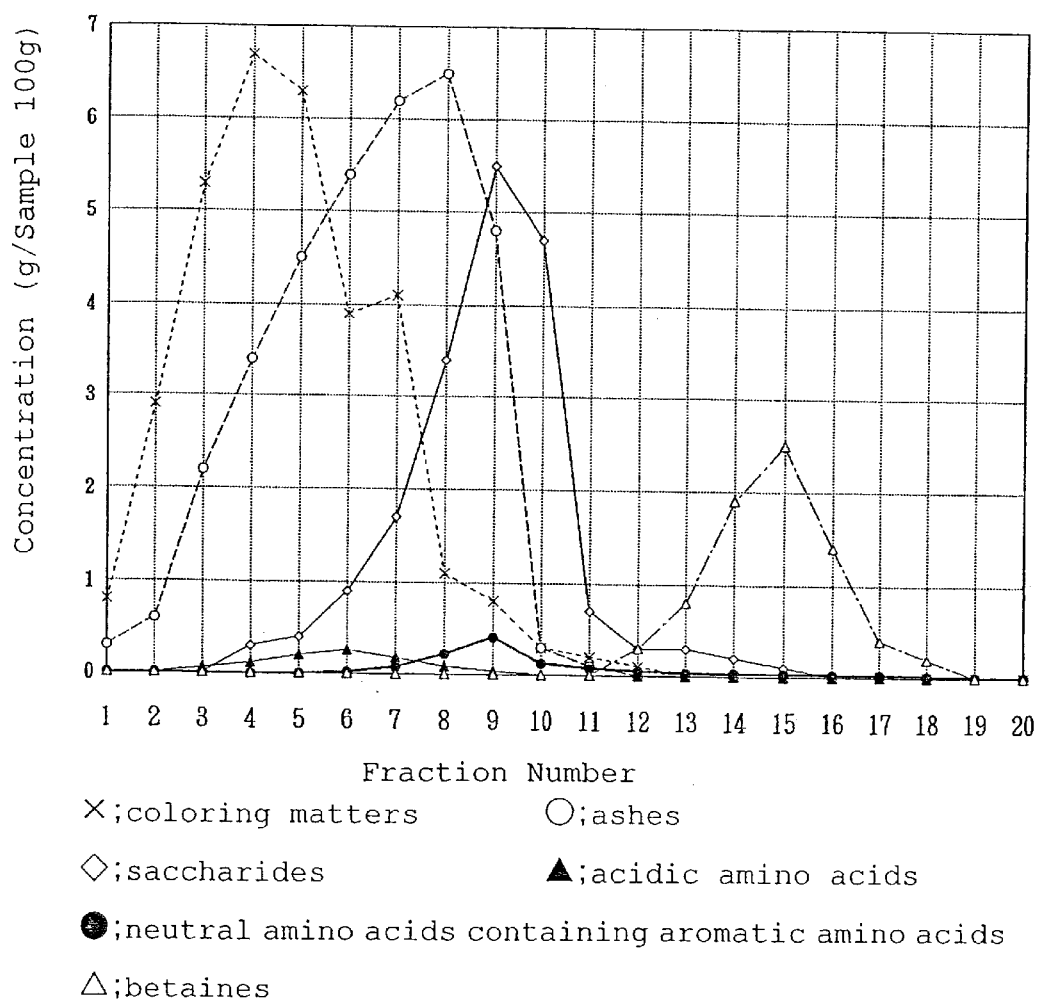
FIG. 1 is a graph showing a relationship between respective fractions which flow out of a first-step first resin layer and concentrations of respective ingredients contained in an effluent.

DESCRIPTION OF REFERENCE NUMERALS 1 to 8: First to eighth resin towers
F1: A supply cock for a raw material solution
F2-1, F2-2, F2-3, F2-4: Supply cocks for fractions C and D of a second circulation system
E1 to E4: Supply cocks for eluent (1)
E5 to E8: Supply cocks for eluent (2)
R1: Cocks relating to a first circulation system
P1: A pump of the first circulation system
S1: A cock for taking out fractions C and D of the first circulation system into a tank
S2: A cock for shutting off the first circulation system
R2: A cock relating to the second circulation system
P2: A pump of the second circulation system
A1 to A4: Cocks for recovering fraction A
B1 to B4: Cocks for recovering fraction B
C1 to C4: Cocks for recovering fraction C
D1 to D4: Cocks for recovering fraction D

DETAILED DESCRIPTION OF THE INVENTION

The mixed solutions used as raw materials in the method for recovering amino acids according to the present invention include CR waste liquor which is residues after recovery of effective ingredients from molasses by CR treatment, resin waste liquor which is regeneration waste liquor of ion exchange resins used for purification of sugar liquid in the process of sugar manufacture, yeast production waste liquor in bread manufacture, and alcoholic fermentation waste liquor. Mixed solutions similar in composition to these can be used as raw materials. Usually, these mixed solutions have an rBx (refractometric Brix Degree; a solid percentage measured by the refractive index) of 50 to 60, a cation concentration of 0.5 to 3.0 N and an anion concentration of 0.4 to 2.8 N. Further, these mixed solutions contain 0 to 60 g of saccharides, 1.0 to 2.0 g of the total amino acids, 0 to 30 g of betaines, and a certain amount of coloring matters, per 100 g of solid matter.

In the amino acids contained in sugar beets, usually, the acidic amino acids include aspartic acid and glutamic acid, the neutral amino acids include threonine, serine, glycine, alanine, valine, leucine, isoleucine, methionine and γ-amino butyric acid (GABA), the aromatic amino acids include tyrosine and phenylalanine, and the basic amino acids include histidine, lysine and arginine. Accordingly, when the CR waste liquor is used as the mixed solution comprising inorganic acid salts, coloring matters, ashes, betaines, amino acids and non-electrolytes including saccharides, the above-mentioned neutral amino acids, particularly valine, leucine, isoleucine and GABA, and the aromatic amino acids, particularly tyrosine, can be recovered according to the present invention.

The resin layer comprising the Na type or K type IER, the resin layer comprising the $NH_4$ type IER, the resin layer comprising the Ca type IER, and the resin layer comprising the Mg type IER are hereinafter referred to as a first resin layer, a second resin layer, a third resin layer and a fourth resin layer, respectively.

As the resins used for the first resin layer (Na type or K type IER) of the present invention, there are employed resins which allow neutral amino acids to be well separable from the other ingredients (such as ashes, coloring matters, betaines and acidic amino acids). As the strongly acidic ion exchange resins used for the third resin layer (Ca type IER) and the fourth resin layer (Mg type IER), there are employed resins having good separability for individual neutral amino acids. Thus, resins depending on the amino acids to be recovered are suitably selected. As these resins, there are usually used strongly acidic ion exchange resins in which polystyrene resins crosslinked with divinylbenzene are sulfonated. The degree of crosslinking is from 3% to 10%, and preferably from 5% to 8%. It is preferred that the ion exchange resins used for the first, third and fourth resin layers of the present invention have a uniform particle size for improving the separation performance. Although the particle size ranges from 210 to 450 μm, it varies depending on the amino acid to be recovered and the maker of the CR resin. Further, one of the conditions for selecting the resins is physical durability.

The resins used in the present invention include, for example, Amberlite CG6000, CR1310Na (manufactured by ORGANO CORPORATION), Dowex chromatographic separation resin 99K-320, XFS-43279 (manufactured by Dow Chemical Japan Limited) and DIAION UBK530 (manufactured by MITSUBISHI CHEMICAL CORPORATION).

These resins can be substituted by other alkali metal type strongly acidic ion exchange resins. However, the effect of substitution is little from the economical viewpoint.

Strongly acidic ion exchange resins comprising sulfone group-containing polystyrene crosslinked in a degree of 7% to 10% by divinylbenzene are generally used for the $NH_4$ type IER of the second resin layer of the present invention. For example, Dowex HCR-W2 (manufactured by Dow Chemical Japan Limited) and DIAION SK1B (manufactured by MITSUBISHI CHEMICAL CORPORATION) are used. In this second resin layer, the adsorption-fixed bed system is usually employed.

The operation system of the first, third and fourth resin layers may be any of the fixed bed system, the simulated moving bed system and a combination thereof. In particular, a combination of a new JO (multiple ingredient separation) system of ORGANO CORPORATION or a new MCI (three ingredient separation) system of MITSUBISHI CHEMICAL CORPORATION with the general simulated moving bed system is preferred as a system which can efficiently separate multiple ingredients of amino acids. The above-mentioned new JO system is described in U.S. Pat. No. 5,198,120, and the above-mentioned new MCI system is described in Japanese Patent Laid-Open Publication (Hei) 7-232003.

The operating temperature of the first, third and fourth resin layers of the present invention is preferably from 60 to 90° C., and more preferably about 80° C. Less than 60° C. causes the problem of pollution caused by microorganisms, whereas exceeding 90° C. results in increased deterioration of the resins.

Further, for the operating temperature of the second resin layer of the present invention, solution passage and regeneration are both performed at room temperature.

Recovering Method 1

A recovering method using the first resin layer (Na type or K type IER) as the first-step resin layer and the second resin layer ($NH_4$ type IER) as the second-step resin layer will be described as recovering method 1.

In the Na type or K type IER of the first resin layer, inorganic salts and acidic materials are first eluted without being adsorbed, due to the repulsion of cation in the solution for sodium ions or potassium ions adsorbed in the resin, and no adsorption of anion with resins. As a result, the pH of an effluent increases after elution of inorganic salts and acidic materials.

Although water or an aqueous solution of a caustic alkali is used as an eluent from the above-mentioned first resin layer, an aqueous solution of sodium hydroxide having a pH of 8.5 to 11, preferably 9.5 to 10.5, is usually used. When this eluent is used, (1) coloring matters, (2) acidic amino acids, (3) ashes, (4) neutral amino acids and saccharides and (5) betaines usually flow out in this order. As a result, the first fraction in the effluent mainly contains coloring matters, acidic amino acids and ashes, the second fraction mainly contains neutral amino acids and saccharides, and the third fraction mainly contains betaines.

This invention will be illustrated with reference to FIGS. 1 to 12 in details below, but the following disclosure shows preferred embodiments of the invention and is not intended to limit the scope of the invention.

In FIGS. 1 to 10, the supply rate of the raw material solution supplied to a first resin layer was 5.56% of the apparent volume of the resin layer. In FIGS. 1 to 10, the amount of each fraction is 8.01 ml (2.67% of the apparent volume of the resin layer).

FIG. 1 shows a relationship between respective fractions and concentrations of respective ingredients contained in the effluent, which is obtained by supplying CR waste liquor to the first resin layer. The effluent can be separated into three fractions: a first fraction (fraction numbers 1 to 6), a second fraction (fraction numbers 7 to 11) and a third fraction (fraction numbers 12 to 20).

Figure 2:
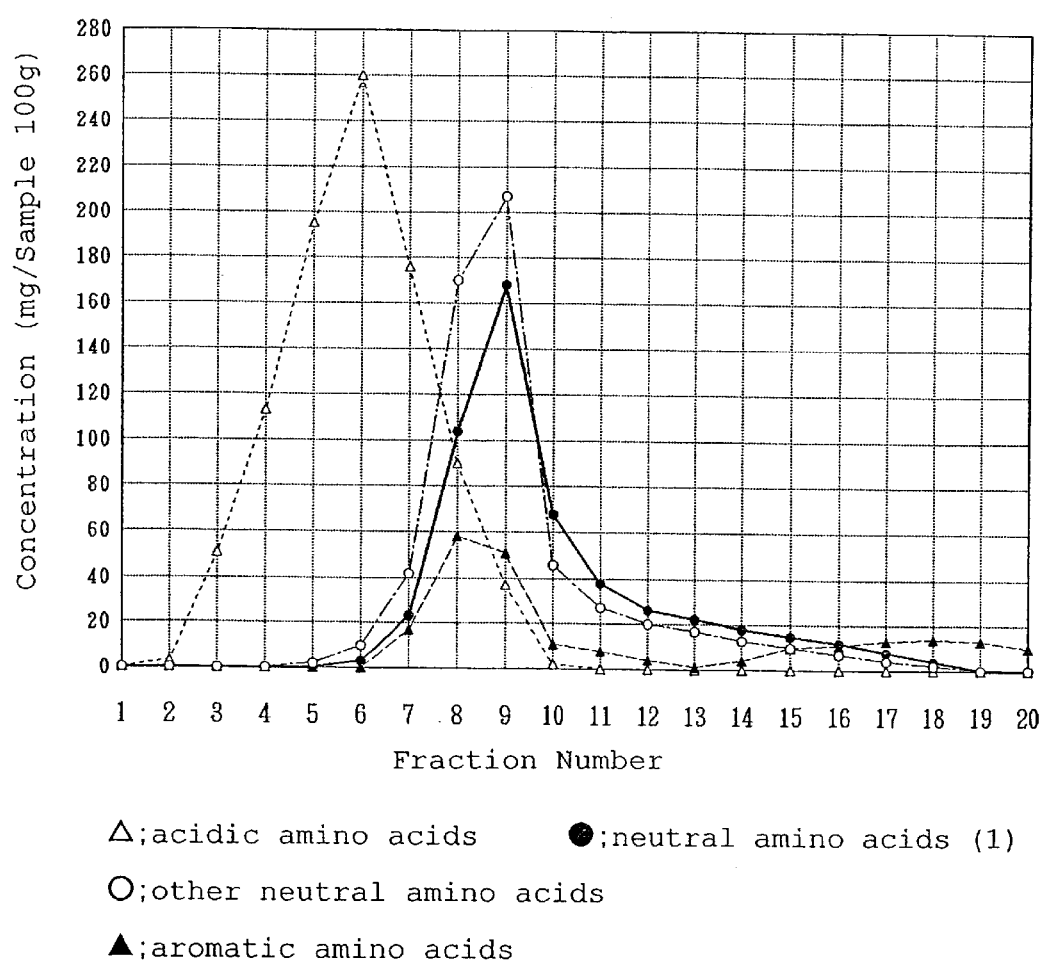
FIG. 2 is a graph showing a relationship between respective fractions which flow out of a first-step first resin layer and concentrations of respective amino acids based on the total amino acids contained in an effluent.

FIG. 2 shows a relationship between respective fractions and concentrations of respective amino acids contained in the effluent, which is obtained by supplying CR waste liquor to the first resin layer.

In recovering method 1, the effluent of the second fraction mainly containing neutral amino acids and saccharides, which flows out of the above-mentioned first resin layer, is supplied to the second resin layer comprising the ammonium type strongly acidic ion exchange resin. An aqueous solution of ammonia is applied to this second resin layer as an eluent to elute and recover amino acids mainly comprising neutral amino acids adsorbed by the resin layer. The aqueous solution of ammonia used is preferably aqueous ammonia having a concentration of 1 N to 2 N.

An effluent containing the neutral amino acids in this eluent is concentrated and adjusted to pH 5.7, thus obtaining crystallized tyrosine, an aromatic amino acid. The purity of tyrosine thus obtained is usually from 90% to 100% by weight, and the recovery thereof is usually from 30% to 60% by weight (based on tyrosine contained in the raw material).

A filtrate from which tyrosine is separated by filtration is decolorized, concentrated and crystallized or pulverized, which allows neutral amino acids other than tyrosine (such as leucine, isoleucine, valine, serine and GABA) to be recovered. The total content of leucine, isoleucine and valine thus obtained is usually from about 30% to about 50% by weight based on a mixture of the neutral amino acids, and the recovery of the neutral amino acids is usually from 60% to 70% by weight (based on the neutral amino acids contained in the raw material).

Recovering Method 2

A recovering method using the first resin layer (Na type or K type IER) as the first-step resin layer and the third resin layer (Ca type IER) as the second-step resin layer will be described as recovering method 2.

In recovering method 2, of the above-mentioned three fractions obtained from the first resin layer, the effluent of the second fraction is supplied to the third resin layer comprising the Ca type IER, and elution is conducted using water as an eluent, thereby obtaining desired amino acids.

In the Ca type IER of the third resin layer, the saccharides are completely separated from the amino acids, and the amino acids are further subdivided. The reason for this is considered to be as follows. That is to say, the calcium type strongly acidic ion exchange resin is poor in ion exclusion ability and shows poor molecular sieve effect, but is excellent in ligand exchange ability, so that the saccharides can be completely separated from the neutral amino acids and the aromatic amino acids. Further, the individual neutral amino acids can also be separated by means of dividing the obtained effluent into different fractions each containing different concentration peaks.

In general, different from using Na type IER, when the content of salts is high in the raw material, inorganic salts and acidic materials are hard to be eluted first from the Ca type IER owing to Ca type IER's poor ion exclusion ability. Thus, the pH of the solution in the resin layer hardly changes stepwise (such as neutral first, then, low pH, and finally high pH), resulting in instability of a change in charge of amino acids.

Further, when the concentration of cations other than calcium is high, the type of resin varies to result in insufficient separation of amino acids from saccharide or insufficient separation into each amino acid.

However, the present invention brings no problem, because salts and cations are previously removed in the first resin layer.

In the above-mentioned third resin layer, water used as the eluent includes pure water, distilled water and deionized water, and preferred is boiled ion-exchanged water.

Of the fractions of the effluent from the first resin layer, the second fraction is supplied to the third resin layer, and the above-mentioned eluent is further allowed to flow therein to fractionate an effluent of the third resin layer, thereby roughly dividing the effluent into two fractions: a first fraction mainly containing saccharides and a second fraction mainly containing neutral amino acids.

Figure 3:
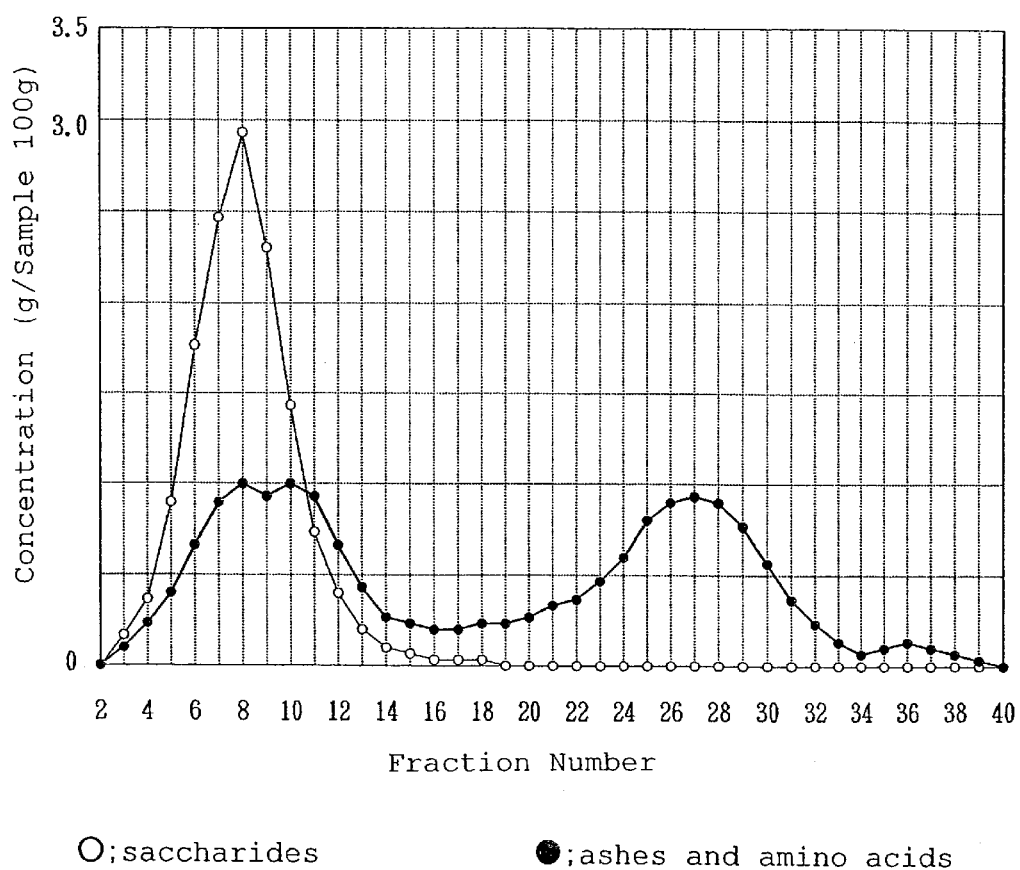
FIG. 3 is a graph showing a relationship between respective fractions which flow out of a second-step third resin layer and concentrations of saccharides, amino acids and ashes contained in an effluent.
Figure 4:
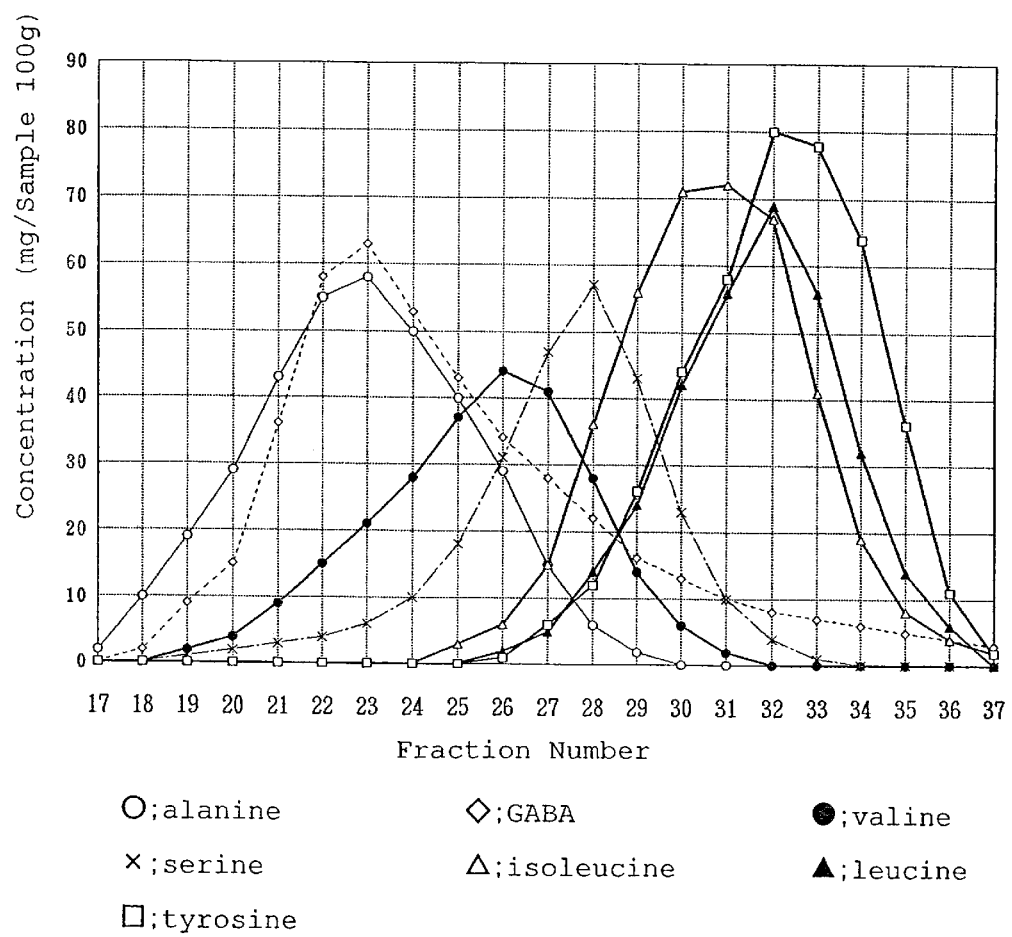
FIG. 4 is a graph showing a relationship between respective fractions which flow out of a second-step third resin layer and concentrations of respective amino acids based on the total amino acids contained in an effluent.

FIG. 3 shows a relationship between the respective fractions of the effluent obtained by supplying the second fraction of the effluent from the first resin layer to the third resin layer and concentrations of saccharides, amino acids and ashes contained in the effluent. Further, FIG. 4 shows a relationship between the respective fractions of the effluent from the third resin layer and concentrations of the respective amino acids based on the total amino acids contained in the effluent.

The neutral amino acid-containing fraction (the second fraction: fraction numbers 17 to 37) separated from the saccharide-containing fraction (the first fraction: fraction numbers 2 to 16) is concentrated, and the pH thereof is adjusted to obtain crystallized tyrosine. The purity of tyrosine thus obtained is usually from 90% to 100% by weight, and the recovery thereof is usually from 30% to 60% by weight (based on tyrosine contained in the raw material).

A filtrate from which tyrosine is separated by filtration is decolorized, concentrated and crystallized or pulverized, which allows neutral amino acids other than tyrosine (such as leucine, isoleucine, valine, serine and GABA) to be recovered. The total content of leucine, isoleucine and valine thus obtained is usually from about 45% to about 60% by weight based on a mixture of the neutral amino acids, and the recovery of the neutral amino acids is usually from 50% to 70% by weight (based on the neutral amino acids contained in the raw material).

Recovering Method 2-2

The fraction shown in FIG. 4 may be further subdivided into a first fraction (fraction numbers 13 to 19) containing saccharides, amino acids and ashes, a second fraction (fraction numbers 20 to 24) containing GABA, alanine and valine, a third fraction (fraction numbers 25 to 31) containing serine and valine, and a fourth fraction (fraction numbers 32 to 37) containing leucine, isoleucine and tyrosine.

The above-mentioned third fraction may be combined with the above-mentioned fourth fraction to a fraction (fraction numbers 25 to 37) containing serine, valine, leucine, isoleucine and tyrosine.

The effluent of the above-mentioned second fraction is decolorized, concentrated and crystallized or pulverized, which allows a mixture of neutral amino acids containing GABA, alanine and valine to be recovered.

The effluent of the above-mentioned third fraction is decolorized, concentrated and crystallized or pulverized, which allows a mixture of neutral amino acids containing serine and valine to be recovered.

Further, the effluent of the above-mentioned fourth fraction is concentrated, and the pH thereof is adjusted to obtain crystallized tyrosine. A mixture of neutral amino acids containing leucine and isoleucine is obtained from the filtrate.

Recovering Method 2-2-A

In recovering method 2-2-A, the second fraction or the third fraction of the effluent from the third resin layer in the above-mentioned recovering method 2-2 is further supplied to the fourth resin layer (Mg type IER), and various amino acids are recovered using water as an eluent in the same manner as with the third resin layer.

The Mg type IER of the fourth resin layer has the effect that the elution order of neutral amino acids is different from that in the Ca type IER, so that the composition of recovered fractions of amino acids can be changed.

For the purpose of recovering GABA, the effluent of the second fraction (fraction numbers 20 to 24) in FIG. 4 is used as the fractionated effluent obtained from the third resin layer of the recovering method 2-2. The effluent within this range is a GABA-, alanine- and valine-rich fraction.

Figure 5:
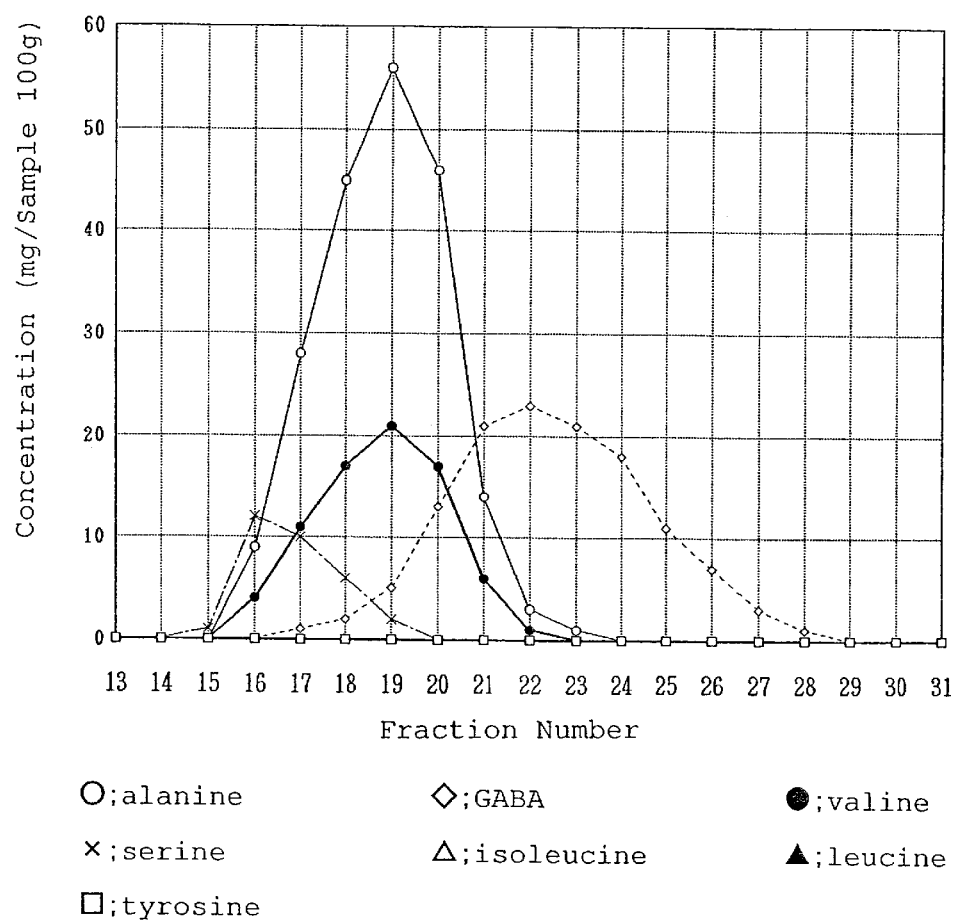
FIG. 5 is a graph showing a relationship between respective fractions of a GABA(γ-amino butyric acid)-rich fraction which flows out of a third-step fourth resin layer and concentrations of respective amino acids based on the total amino acids contained in an effluent.

FIG. 5 shows a relationship between the respective fractions of the effluent obtained by supplying the effluent within the range of fraction numbers 20 to 24 in FIG. 4 to the fourth resin layer and concentrations of the respective amino acids based on the total amino acids contained in the effluent.

The effluent of fraction numbers 22 to 28 of FIG. 5 can be recovered and concentrated to obtain a concentrated solution or a powdery solid of GABA. The purity of GABA thus obtained is usually from about 80% to about 100% by weight, and the recovery thereof is usually from 10% to 40% by weight (based on GABA contained in the raw material).

Further, the effluent of fraction numbers 15 to 21 of FIG. 5 can be recovered and concentrated to obtain a concentrated solution or a powdery solid of a mixture containing alanine, valine and serine.

Furthermore, for the purpose of recovering valine, the effluent (the third fraction; within the range of fraction numbers 25 to 31) in FIG. 4 is used as the fractionated effluent obtained from the third resin layer of the recovering method 2-2. The effluent within this range is a valine- and serine-rich fraction.

Figure 6:
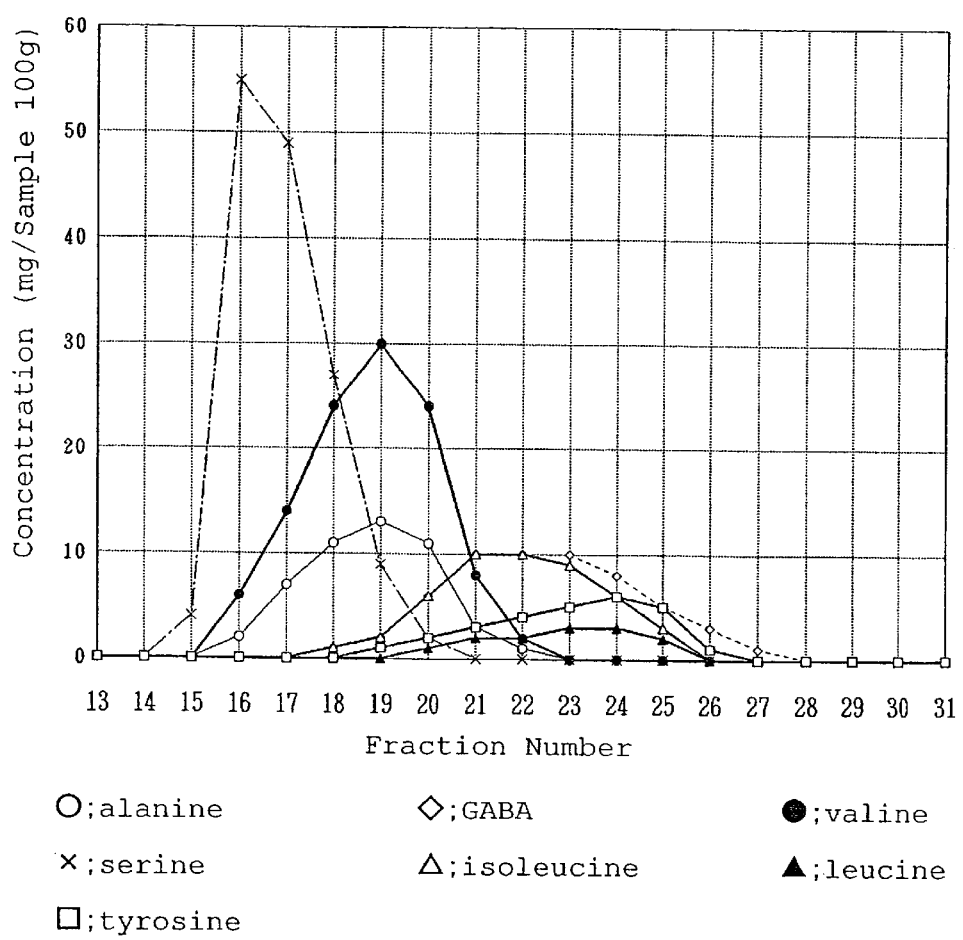
FIG. 6 is a graph showing a relationship between respective fractions of a valine-rich fraction which flows out of a third-step fourth resin layer and concentrations of respective amino acids based on the total amino acids contained in an effluent.

FIG. 6 shows a relationship between the respective fractions of the fraction obtained by supplying the effluent within the range of fraction numbers 25 to 31 in FIG. 4 to the fourth resin layer and concentrations of the respective amino acids based on the total amino acids contained in the effluent.

The effluent of fraction numbers 19 to 21 of FIG. 6 can be recovered and concentrated to obtain a concentrated solution or a powdery solid of valine. The purity of valine thus obtained is usually from about 40% to about 60% by weight, and the recovery thereof is usually from 10% to 30% by weight (based on valine contained in the raw material).

Further, the effluent of fraction numbers 15 to 18 of FIG. 6 can be recovered and concentrated to obtain a concentrated solution or a powdery solid of serine.

Recovering Method 3

A recovering method using the first resin layer (Na type or K type IER) as the first-step resin layer and the fourth resin layer (Mg type IER) as the second-step resin layer will be described as recovering method 3. In recovering method 3, the effluent of the second fraction obtained from the first resin layer is supplied to the fourth resin layer, and allowed to flow out using water as an eluent, thereby roughly dividing the effluent into two fractions: a first fraction (fraction numbers 3 to 14) mainly containing saccharides and a second fraction (fraction numbers 15 to 28) mainly containing neutral amino acids and ashes.

Figure 7:
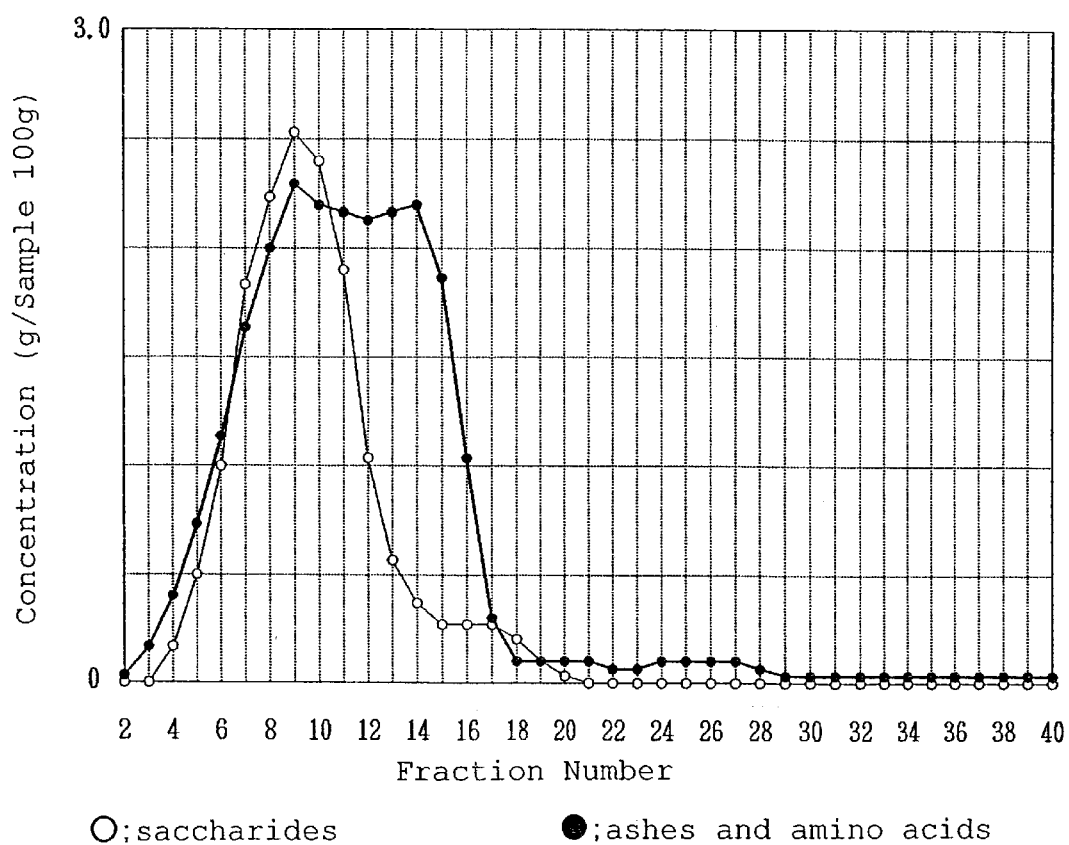
FIG. 7 is a graph showing a relationship between respective fractions which flow out of a second-step fourth resin layer and concentrations of saccharides, amino acids and ashes contained in an effluent.
Figure 8:
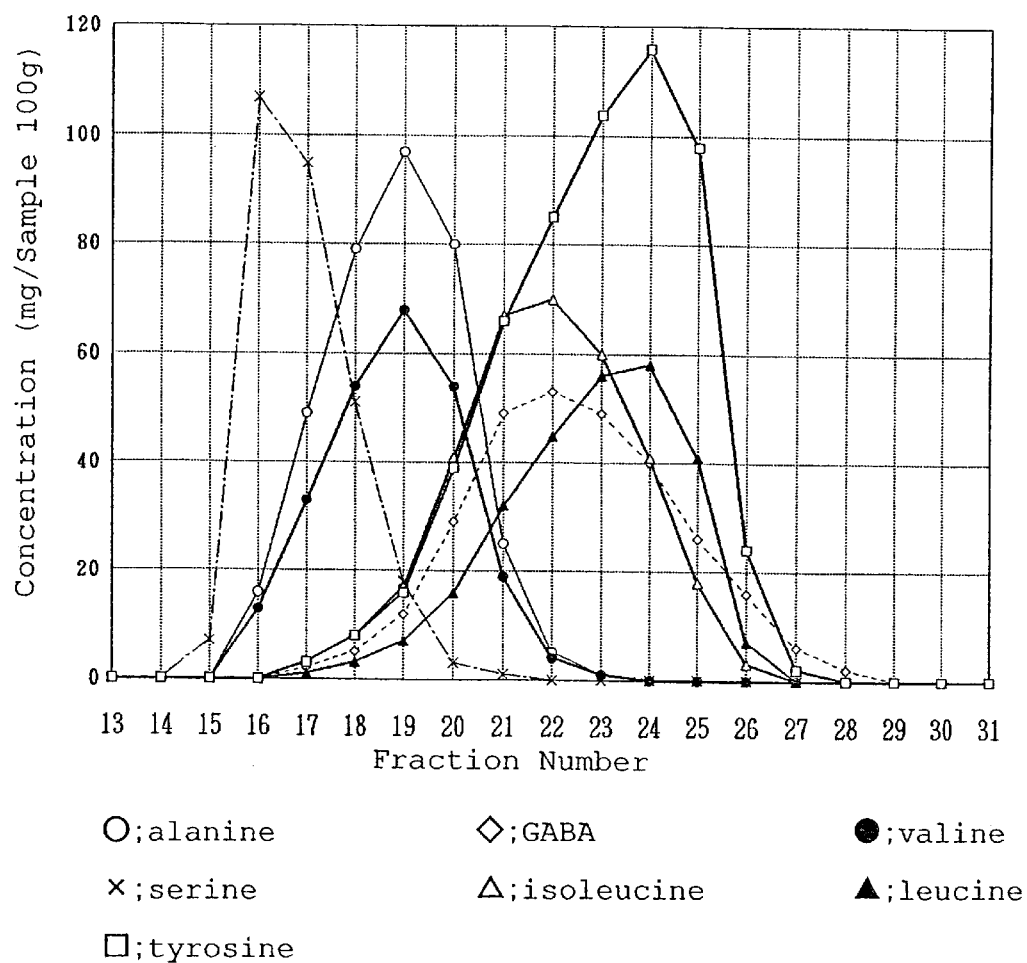
FIG. 8 is a graph showing a relationship between respective fractions which flow out of a second-step fourth resin layer and concentrations of respective amino acids based on the total amino acids contained in an effluent.

FIG. 7 shows a relationship between the respective fractions of the effluent obtained by supplying the effluent of the second fraction allowed to flow out of the first resin layer to the fourth resin layer and concentrations of saccharides, amino acids and ashes contained in the effluent. Further, FIG. 8 shows a relationship between the respective fractions of the effluent eluted from the fourth resin layer and concentrations of the respective amino acids contained in the effluent.

The fraction containing neutral amino acids separated from saccharides (the second fraction: fraction numbers 15 to 28) is concentrated, and the pH thereof is adjusted to obtain crystallized tyrosine. The purity of tyrosine thus obtained is usually from 90% to 100% by weight, and the recovery thereof is usually from 30% to 50% by weight (based on tyrosine contained in the raw material).

A filtrate from which tyrosine is separated by filtration is decolorized, concentrated and crystallized or pulverized, which allows neutral amino acids other than tyrosine (such as leucine, isoleucine, valine, serine and GABA) to be recovered. The total content of leucine, isoleucine and valine thus obtained is usually from about 40% to about 50% by weight based on the neutral amino acids contained in the raw material, and the recovery of the neutral amino acids is usually from 40% to 70% by weight (based on the neutral amino acids contained in the raw material).

Recovering Method 3-2

The fraction shown in FIG. 7 may be further subdivided into a first fraction (fraction numbers 1 to 14) containing saccharides, amino acids and ashes, a second fraction (fraction numbers 15 to 17) containing serine, a third fraction (fraction numbers 18 to 21) containing alanine and valine, and a fourth fraction (fraction numbers 22 to 28) containing tyrosine, leucine, isoleucine and GABA.

The above-mentioned second fraction may be combined with the above-mentioned third fraction to a fraction containing serine, alanine and valine. In that case, the neutral amino acid-containing fraction is divided into two fractions: a fraction containing serine, alanine and valine and a fraction containing tyrosine, leucine and isoleucine.

The effluent of the above-mentioned second fraction is decolorized, concentrated and crystallized or pulverized, which allows a mixture of neutral amino acids containing serine to be recovered.

The effluent of the above-mentioned third fraction is decolorized, concentrated and crystallized or pulverized, which allows a mixture of neutral amino acids containing alanine and valine to be recovered.

Recovering Method 3-2-A

In recovering method 3-2-A, the third fraction or the fourth fraction of the effluent from the fourth resin layer in the above-mentioned recovering method 3 is further supplied to the third resin layer (Ca type IER), and various amino acids are recovered using water as an eluent.

Figure 9:
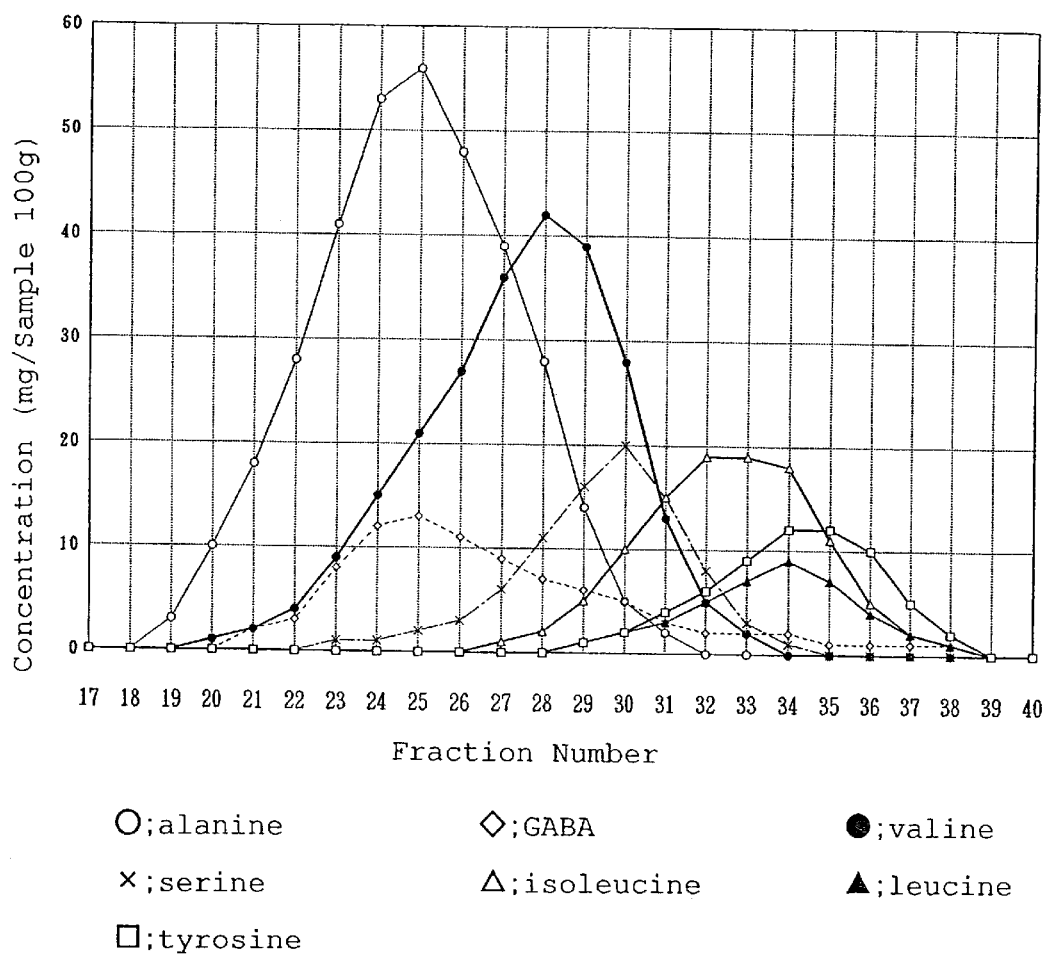
FIG. 9 is a graph showing a relationship between respective fractions of a valine-rich fraction which flows out of a third-step third resin layer and concentrations of respective amino acids based on the total amino acids contained in an effluent.

For the purpose of recovering valine, the effluent of the third fraction (fraction numbers 18 to 21) in FIG. 8 is used as the fractionated effluent obtained from the fourth resin layer of the recovering method 3-2. The effluent within this range is an alanine- and valine-rich fraction. FIG. 9 shows a relationship between the respective fractions of the effluent obtained by supplying the effluent within the range of fractions 18 to 21 in FIG. 8 to the third resin layer and concentrations of the respective amino acids based on the total amino acids contained in the effluent.

The effluent of fraction numbers 28 to 31 of FIG. 9 can be recovered and concentrated to obtain a concentrated solution or a powdery solid of valine. The purity of valine thus obtained is usually from about 30% to about 60% by weight, and the recovery thereof is usually from 10% to 40% by weight (based on valine contained in the raw material).

Further, the effluent of fraction numbers 19 to 26 of FIG. 9 can be recovered and concentrated to obtain a concentrated solution or a powdery solid of alanine.

Figure 10:
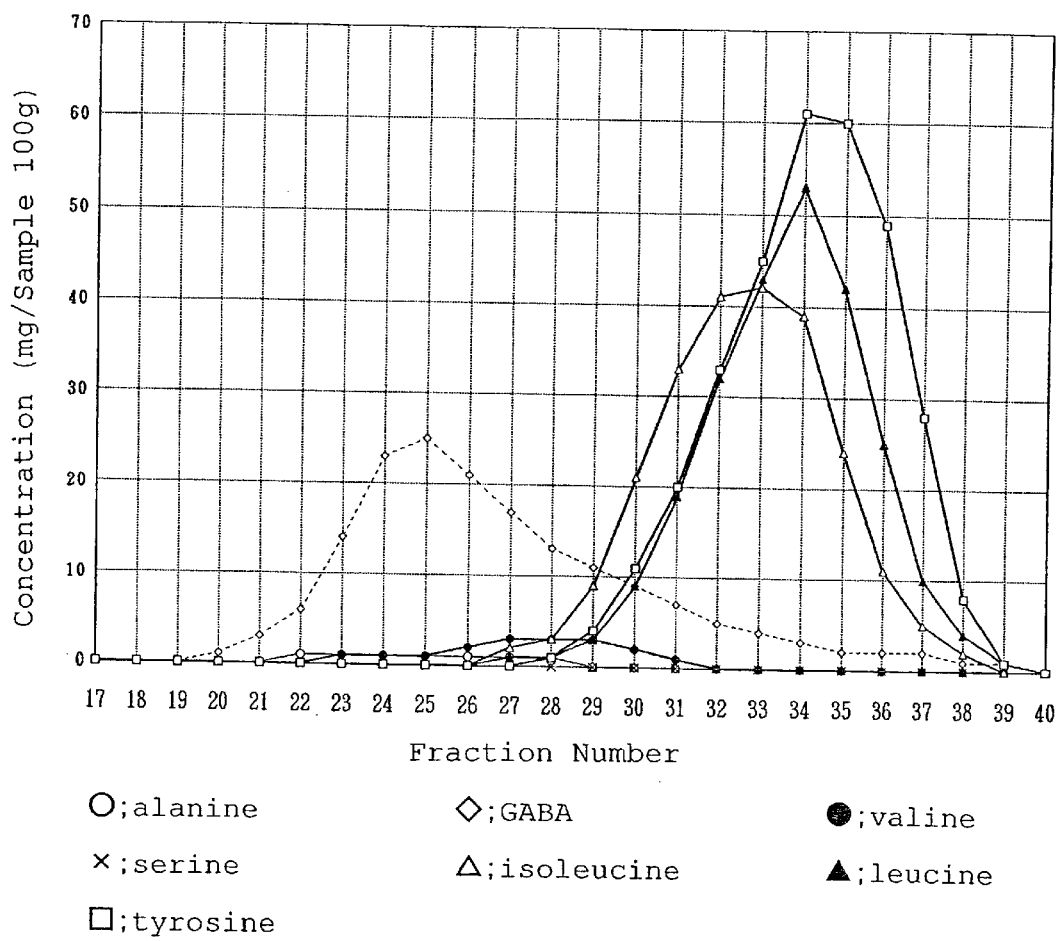
FIG. 10 is a graph showing a relationship between respective fractions of a GABA-rich fraction which flows out of a third-step third resin layer and concentrations of respective amino acids based on the total amino acids contained in an effluent.

For the purpose of recovering GABA, the effluent of the fourth fraction (fraction numbers 22 to 28) in FIG. 8 is used as the fractionated effluent obtained from the fourth resin layer of the recovering method 3-2. The effluent within this range is a tyrosine-, leucine-, isoleucine- and GABA-rich fraction. FIG. 10 shows a relationship between the respective fractions of the effluent obtained by supplying the effluent within the range of fractions 22 to 28 in FIG. 8 to the third resin layer and concentrations of the respective amino acids based on the total amino acids contained in the effluent.

The effluent of fraction numbers 20 to 27 of FIG. 10 can be recovered and concentrated to obtain GABA. The purity of GABA thus obtained is usually from about 80% to about 100% by weight, and the recovery thereof is usually from 20% to 40% by weight (based on GABA contained in the raw material).

Further, the effluent of fraction numbers 29 to 39 of FIG. 10 is recovered and concentrated, and the pH thereof is adjusted to obtain crystallized tyrosine.

A filtrate from which tyrosine is separated by filtration is decolorized, concentrated and crystallized or pulverized, which allows neutral amino acids other than tyrosine (leucine and isoleucine) to be recovered.

In the recovering method of the present invention, the effluents supplied to the second to forth resin layers may be used as such or after concentration. The resulting amino acid-containing effluents can be concentrated, pH adjusted and recrystallized by conventional methods to obtain highly concentrated amino acid solutions or crystallized amino acids (solid or powdery).

In the present invention, for example, in the case of recovering method 2, a separation system described in Example 7 given later is the new JO (multiple ingredient separation) system for the first resin layer, and the simulated moving bed system for the third resin layer. A combination thereof is suitable for separation recovery of a mixture of neutral amino acids and tyrosine.

Similarly, in the case of recovering method 2-2-A or 3-2-A, the new JO (multiple ingredient separation) system can be applied to three systems: the first-step first resin layer, the second-step fourth or third resin layer, and the third-step fourth or third resin layer. In that case, the application of the new JO system thereto makes it possible to continuously separate desired amino acids. When circulation systems of the first resin layer, the third resin layer and the fourth resin layer are each constituted, the amino acids are further subdivided, and the desired amino acids can be recovered by separation. This is therefore suitable for the industrial recovery of the individual amino acids.

Figure 12:
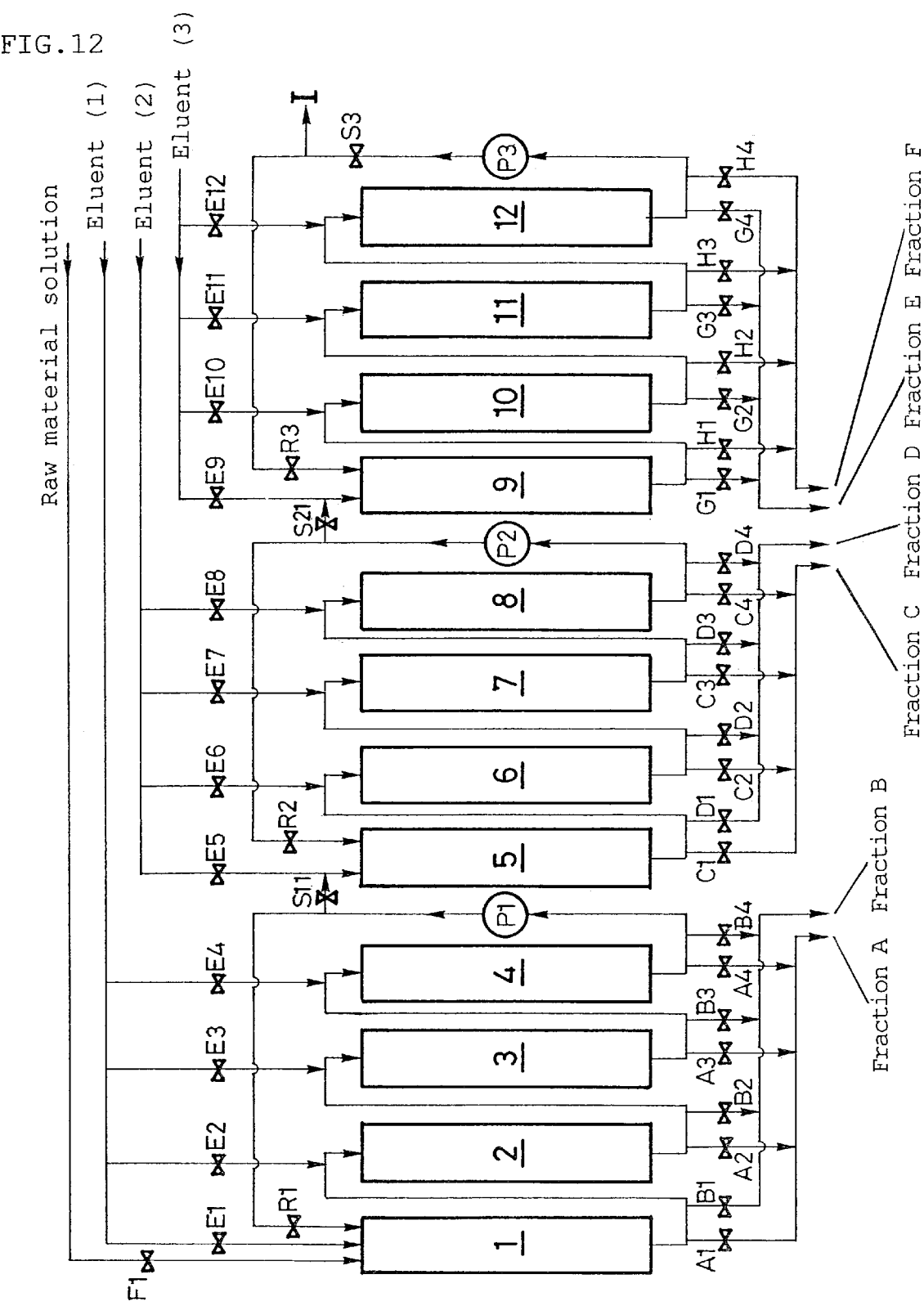
FIG. 12 is a schematic block diagram showing an example of an apparatus which can be used in recovering method 3-2A.

One embodiment thereof will be illustrated with reference to FIG. 12. First, second and third circulation systems are formed by resin layers 1 to 4, resin layers 5 to 8 and resin layers 9 to 12, respectively. A raw material solution is introduced into a first resin layer (Na type or K type IER), and separated into three fractions in the first circulation system. Two fractions of them are discharged outside the first circulation system to recover them. The remaining one fraction is introduced into the resin layer 5 of the second circulation system, and further fractionated into three fractions. Similarly to the first circulation system, two fractions are discharged outside the second circulation system to recover them. The remaining one fraction is introduced into the resin layer 9 of the third circulation system, and divided into three fractions to recover the respective fractions. Thus, the separated amino acids can be recovered.

The present invention has the constitution and function as described above. It becomes therefore possible to recover the neutral amino acids and aromatic amino acids extremely high in market value from the solutions containing trace amounts of amino acids in highly concentrated inorganic acid salts, or highly concentrated non-electrolytes such as saccharides, for example, CR waste liquor and resin waste liquor which have hitherto been subjected to the activated sludge process and discarded, or only condensed for utilization as organic fertilizer, in beet sugar manufacturing factories. Accordingly, the present invention contributes largely to the environmental protection and the industrial development.

DESCRIPTION OF THE PREFERRED EMBODIMENTS

This invention will be illustrated with reference to examples in more details below, but the following disclosure shows preferred embodiments of the invention and is not intended to limit the scope of the invention. Parts and percentages used in the examples are by weight, unless otherwise specified.

EXAMPLE 1 (Recovery of Second Fraction)

As a raw material, CR waste liquor ("CCR" manufactured by NIPPON BEET SUGAR MFG. CO., LTD.) was used. This liquor had an rBx of 25, a cation concentration of 1.06 N, an anion concentration of 0.91 N and a pH of 10.0, and contained 33.6 g of saccharides, 12.3 g of betaines and 4.8 g of the total amino acids, per 100 g of solid matter. This raw material solution was supplied to a first resin layer comprising 300 ml of an Na type IER ("Amberlite CG6000" manufactured by ORGANO CORPORATION) at 80° C. at a space velocity of 0.6 ml/ml·min. The supply rate thereof was 5.56% of the apparent volume of the resin layer. Then, an aqueous solution of sodium hydroxide adjusted to pH 10.0 and heated to 80° C. was supplied as an eluent to the first resin layer. Changes in concentrations of respective ingredients to respective fractions collected for every 2.67% 8.01 ml) of the apparent volume of the first resin layer are shown in FIG. 1, and changes in concentrations of respective amino acids are as shown in FIG. 2.

In FIG. 2, the term "neutral amino acids (1)" indicates he total of valine, leucine and isoleucine, and the term "other neutral amino acids" means the total of the other neutral amino acids.

It is known from these figures that neutral amino acids (1) excluding acidic amino acids, and main aromatic amino acids flow out together with saccharides. It is also known from these figures that neutral amino acids (1) and the aromatic amino acids are collectively eluted in fraction numbers 7 to 11 (the range of 13.35% of the apparent volume of the resin layer) It is therefore suitable for the separation of neutral amino acids (1) and the aromatic amino acids to use this range as a second fraction. An effluent of the second fraction contained 20 g of the total amino acids and 72 g of saccharides, per 100 g of solid matter.

EXAMPLE 2 (Recovery of Second Fraction)

Elution was conducted in the same manner as with Example 1 with the exception that pure water and aqueous solutions of sodium hydroxide adjusted to pH 8.5, pH 10.0 and pH 11.0, respectively, were used as eluents for the Na type IER (Amberlite CG6000) to which CR waste liquor was supplied. Changes in concentrations of respective ingredients to respective fractions were examined. As a result, when the pH of the eluents was within the range of 8.5 to 11, preferably 9.5 to 10.5, neutral amino acids (1) and the aromatic amino acids were collectively eluted in fraction numbers 7 to 11, similarly to FIGS. 1 and 2. It was therefore confirmed that the use of fractions within this range as a second fraction was suitable for the separation of neutral amino acids (1) and the aromatic amino acids.

EXAMPLE 3 (Recovery of Second Fraction)

Elution was conducted in the same manner as with Example 1 with the exception that the CR waste liquor having a pH of 10.0 used in Example 1 and the CR waste liquor adjusted to pH 7.5 and pH 8.5 with sulfuric acid were supplied as such to a first resin layer comprising an Na type IER (Dowex monospher 109 manufactured by Dow Chemical Japan Limited) individually. Then, with the same manner as with Example 1, aqueous solutions of sodium hydroxide adjusted to pH 10.0 and heated at 80° C. were used as eluents. As a result, with respect to the pH of the CR waste liquor, the respective amino acids were eluted within a wider fraction range at a lower pH within this range (pH 7.5 to 10.0), which improved the separability of the respective amino acids. Accordingly, the adjustment of the pH of the raw material solution to 7.5 also made it possible to recover the amino acids subdivided for every specific ones.

EXAMPLE 4 (Recovering Method 1; Recovery of Amino Acids)

The effluent of the second fraction obtained in Example 1 contained 20 g of the total amino acids and 72 g of saccharides, per 100 g of solid matter. This second fraction was supplied to a second resin layer comprising 200 ml of an $NH_4$ type IER ("Dowex HCR-W2" manufactured by Dow Chemical Japan Limited) in an amount of 80 times the apparent volume of the resin layer at room temperature at a space velocity of 10 ml/ml·min., thereby allowing the amino acids to be adsorbed. Then, a 1 N aqueous solution of ammonia was introduced into the second resin layer in an amount of 4 times the apparent volume of the resin layer at room temperature at a space velocity of 10 ml/ml·min. to eliminate and recover amino acids mainly comprising neutral amino acids. Such an adsorption-elimination operation increased the purity of the recovered neutral amino acids from 20% to 90%, and the concentration of the neutral amino acids in the effluent from 0.07% to 1.2%.

The above-mentioned recovered solution was concentrated in a concentrating apparatus to 1/5 by volume. As a result, the content of neutral amino acids (1) was 40.3% of the total amino acids. After further adjustment to pH 5.7 with hydrochloric acid, the resulting solution was allowed to stand at room temperature for 12 hours to precipitate tyrosine, an aromatic amino acid, followed by filtration through a membrane filter having an average pore size of 0.45 μm. As a result, the ratio of neutral amino acids (1) to the total amino acids contained in the filtrate increased to 53.8%, which enabled crystallization by further concentration. Further, tyrosine could be recovered from the above-mentioned filter. The purity of tyrosine recovered was 98% by weight, and the recovery thereof was 46% (based on tyrosine contained in the raw material).

A filtrate from which tyrosine was separated by filtration was decolorized, concentrated and crystallized or pulverized, which allowed leucine, isoleucine, valine, serine and GABA of neutral amino acids other than tyrosine to be recovered. The total content of leucine, isoleucine and valine thus obtained was 36% based on the neutral amino acids, and the recovery of the neutral amino acids was 65% (based on the neutral amino acids contained in the raw material).

As described in Example 3, when the pH of the CR waste liquor used as the raw material was up to 7.5, at a lower pH, the respective amino acids were eluted within a wider fraction range, which improved the separability of the respective amino acids. In the above elution, the peaks of the aromatic amino acids such as tyrosine and phenylalanine appeared considerably later than those of the other amino acids. Accordingly, the aromatic amino acids can also be separately recovered by adjusting the pH of the eluent. Accordingly, the adjustment of the pH of the raw material solution also made it possible to recover the amino acids subdivided for every specific ones.

EXAMPLE 5 (Recovering Method 2: Recovery of Second Fraction)

The CR waste liquor was fractionated in the same manner as with Example 1, and fraction numbers 1 to 6 (a solution corresponding to 16.02% of the apparent volume of the resin layer) flowing out after a solution corresponding to the volume of a pipe installed behind the first resin layer was allowed to flow out was taken as a first fraction, fraction numbers 7 to 11 (a solution corresponding to 13.35% of the apparent volume of a resin layer subsequent thereto) as a second fraction, and fraction numbers 12 to 20 (a solution corresponding to 24.03% of the apparent volume of a resin layer subsequent thereto) as a third fraction. Of these, only the second fraction was supplied to a third resin layer comprising 300 ml of an Ca type IER ("Amberlite CG6000" manufactured by ORGANO CORPORATION) at the same solution passage temperature (80° C.), space velocity and supply rate as a solution allowed to flow out of the first resin layer.

EXAMPLE 6 (Recovering Method 2; Recovery of Amino Acids)

Boiled ion-exchanged water was supplied as an eluent (80° C.) to the third resin layer prepared in Example 5. The composition of an effluent allowed to flow out of the third resin layer was as shown in FIGS. 3 and 4 for each fraction number. FIG. 3 shows changes in composition of saccharides, amino acids and ashes with in the range of fraction numbers 2 to 40 of fraction numbers 1 to 42 collected. Of these, fraction numbers 15 to 38 were collected as an amino acid fraction. FIG. 4 shows changes in composition of the respective amino acids within the range of fraction numbers 17 to 37.

After the amino acid fraction obtained from the third resin layer was concentrated to 1/6 by volume, it was adjusted to pH 5.7 with hydrochloric acid. The resulting solution was allowed to stand at room temperature for 24 hours to separate and recover crystallized tyrosine. The recovery of tyrosine was 45% based on tyrosine contained in the raw material, and the purity thereof was 98%. On the other hand, the separated solution was decolorized with activated carbon, followed by concentration and crystallization to obtain powdery neutral amino acids containing leucine and isoleucine as main ingredients and valine, serine and GABA as subsidiary ingredients. The recovery of the resulting powdery neutral amino acids was 56% by weight in total (based on the neutral amino acids contained in the CR waste liquor). Further, the total content of leucine, isoleucine and valine contained in the powdery neutral amino acids was 52% by weight.

EXAMPLE 7 (Recovering Method 2; Recovery of Second Fraction and

Figure 11:
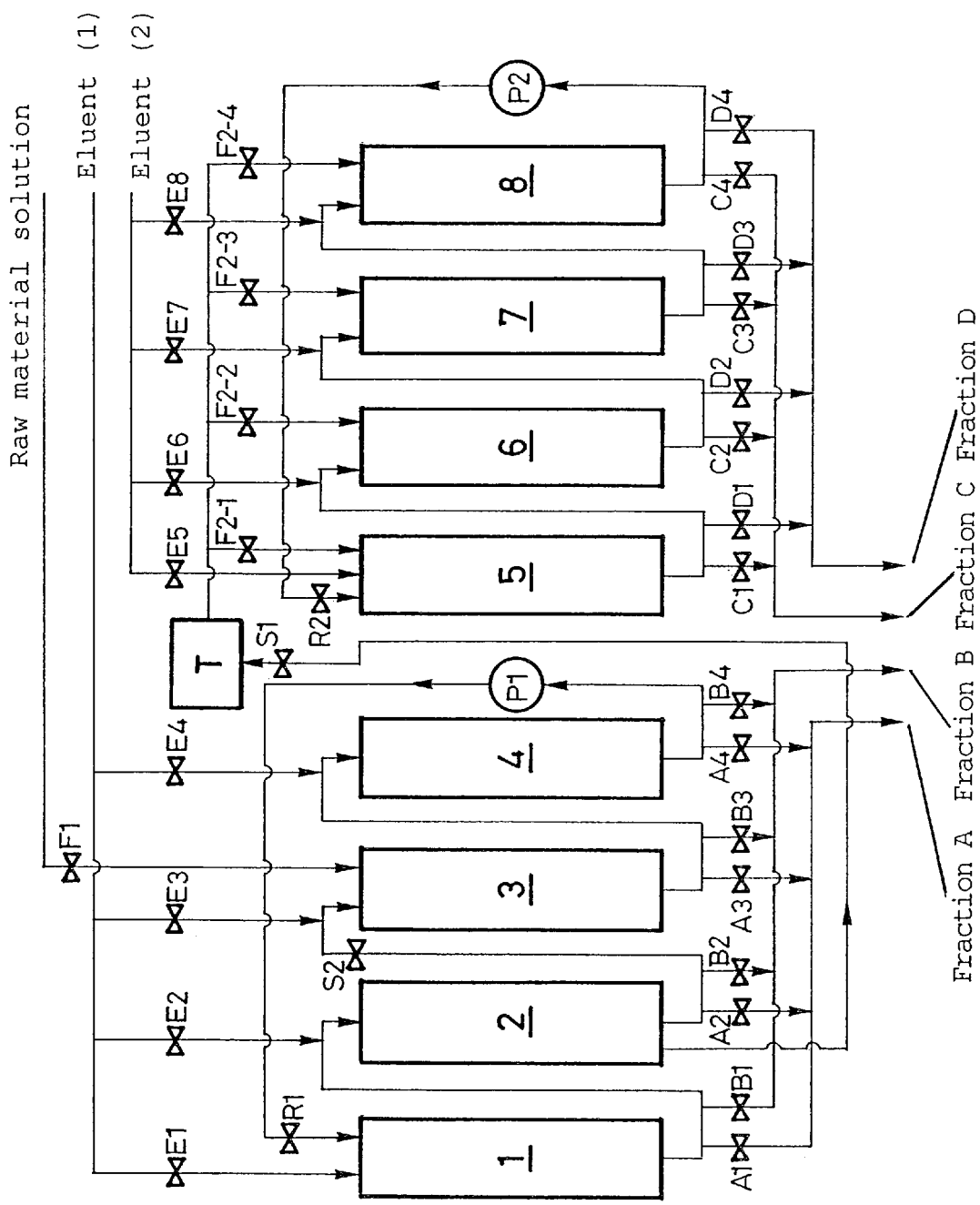
FIG. 11 is a schematic block diagram showing an apparatus used in Example 7.

Recovery of Amino Acids) As shown in FIG. 11, 8 resin towers having an inner diameter of 108.3 mm and a resin layer height of 1,000 mm were arranged. The first to fourth resin towers were filled with an Na type IER ("Amberlite CG6000" manufactured by ORGANO CORPORATION), and an aqueous solution of sodium hydroxide (pH 10.0) was used as an eluent (hereinafter referred to as "eluent (1)"), thereby forming a first circulation system. The fifth to eighth resin towers were filled with a Ca type IER ("Amberlite CG6000" manufactured by ORGANO CORPORATION), and pure water was used as an eluent (hereinafter referred to as "eluent (2)"), thereby forming a second circulation system. Using the first to eighth resin towers, recovering method 2 of the present invention was carried out at a liquid temperature of 80° C.

In the first circulation system, as a preparatory step, a cock F1 was opened to supply 1.61 liters of CR waste liquor ("CCR" manufactured by NIPPON BEET SUGAR MFG.CO., LTD., rBx: 60) as a raw material solution to the third resin tower, and at the same time, the same amount of a liquid in the first resin tower was allowed to flow out through a cock A1. After the raw material solution was introduced into the first circulation system, cocks S2 and R1 were opened, and the all other cocks were closed to circulate the raw material solution through the first to fourth resin towers already filled with eluent (1) with a circulation pump P1, thereby forming a state in which a first fraction (fraction A mainly comprising ashes), a second fraction (a mixed fraction comprising fraction C mainly containing saccharides and fraction D mainly containing neutral amino acids) and a third fraction (fraction B mainly comprising betaines) each formed separated patterns of the fractions, and concentration peaks of the respective fractions were separated.

As a first step, the cock F1, a cock E1, a cock A4 and a cock S1 were opened, and the all other cocks including the cock S2 were closed in a stage in which the concentration peak of fraction A was approximately shifted to the fourth resin tower, the concentration peak of the mixed fraction of fraction C and fraction D to the second resin tower, and the concentration peak of fraction B to the first resin tower, while operating the circulation pump P1. In this state (no circulation flow of towers 1 to 4 was formed), 1.61 liters of the raw material solution was supplied to the third resin tower through the cock F1, and 0.44 liters of fraction A was recovered through the cock A4 at the bottom of the first resin tower. At the same time, 3.90 liters of eluent (1) was supplied to the first resin tower through the cock E1, and 5.06 liters of the mixed fraction of fraction C and fraction D was taken out of the bottom of the second resin tower and once placed in a tank T.

As a second step, the cock R1, a cock E2, a cock B2, the cock S2 and the cock A1 were opened, and the all other cocks of the first circulation system were closed. Eluent (1) was supplied to the second resin tower through the cock E2, fraction B was recovered through the cock B2 at the bottom of the second resin tower, and fraction A was further recovered through the cock A1 at the bottom of the first resin tower, while forming a circulation flow in the first to fourth resin towers.

Then, as a third step, the cock R1, a cock E3, a cock B3, the cock S2 and a cock A2 were opened, and the all other cocks of the first circulation system were closed. Eluent (1) was supplied to the third resin tower through the cock E3, fraction B was recovered through the cock B3 at the bottom of the third resin tower, and fraction A was recovered through the cock A2 at the bottom of the second resin tower, while forming a circulation flow in the first to fourth resin towers.

Further, as a fourth step, the cock R1, a cock E4, a cock B4, the cock S2 and a cock A3 were opened, and the all other cocks of the first circulation system were closed. Eluent (1) was supplied to the fourth resin tower through the cock E4, fraction B was recovered through the cock B4 at the bottom of the fourth resin tower, and fraction A was further recovered through the cock A3 at the bottom of the third resin tower, while forming a circulation flow in the first to fourth resin towers.

Thus, in the second to fourth steps, 2.18 liters of eluent (1) was supplied through each of the cocks E2, E3 and E4, 0.61 liters of fraction A was recovered through each of the cocks A1, A2 and A3, and 1.57 liters of fraction B was recovered through each of the cocks B2, B3 and B4.

According to the above-mentioned first to fourth steps in the first circulation system, the mixed fraction of fraction C and fraction D was once recovered in the tank T, and then, concentrated to about 1/2 by volume. In the present invention, the recovered mixed fraction of fraction C and fraction D may be used as such without concentration. Then, the mixed concentrated fraction was divided into a part for the preparatory step and a part for the subsequent steps. And the each part of the mixed concentrated fraction was introduced into the second circulation system in the manner described as follows. In the preparatory step, the filled solution in the second circulation system was taken out in an amount corresponding to that of the solution introduced.

Further, fraction A and fraction B could be recovered from the first circulation system.

The operating temperature of the first circulation system was 80° C.

In the second circulation system, as a preparatory step, the mixed fraction of fraction C and fraction D of the first circulation system, which was stored in the tank T, was partly introduced into the fifth resin tower of the second circulation system. A cock R2 was opened, the all other cocks including a cock S2 were closed, and a circulation flow was formed in the fifth to eighth resin towers while operating a circulation pump P2, thereby forming a state in which concentration peaks of fraction C mainly comprising saccharides and fraction D mainly comprising neutral amino acids were separated in the fifth resin tower and the seventh resin tower, respectively. The remainder of the mixed fraction in the tank T was divided into four equal parts, which were supplied to the fifth to eighth resin towers, respectively. The subsequent and later steps of the second circulation system required no separation of concentration peaks by circulating an introduced solution in the resin towers, because the concentration peaks were already separated in the preparatory step.

As a first step of the second circulation system, the cock R2, a cock E5, a cock C1 and a cock D3 were opened, and the all other cocks were closed. The mixed solution of fraction C and fraction D was introduced into the seventh resin tower through a cock F2-3, while forming a circulation flow in the fifth to eighth resin towers. At the same time, eluent (2) was supplied to the fifth resin tower through the cock E5. Thus, fraction C was recovered through the cock C1 at the bottom of the fifth resin tower, and fraction D was recovered through the cock D3 at the bottom of the seventh resin tower.

Then, as a second step, the cock R2, a cock E6, a cock C2 and a cock D4 were opened, and the all other cocks were closed. The mixed solution of fraction C and fraction D was introduced into the eighth resin tower through a cock F2-4, while forming a circulation flow in the fifth to eighth resin towers. At the same time, eluent (2) was supplied to the sixth resin tower through the cock E6. Thus, fraction C was recovered through the cock C2 at the bottom of the sixth resin tower, and fraction D was recovered through the cock D4 at the bottom of the eighth resin tower.

Subsequently, as a third step, the cock R2, a cock E7, a cock C3 and a cock D1 were opened, and the all other cocks were closed. The mixed solution of fraction C and fraction D was introduced into the fifth resin tower through a cock F2-1, while forming a circulation flow in the fifth to eighth resin towers. At the same time, eluent (2) was supplied to the seventh resin tower through the cock E7. Thus, fraction C was recovered through the cock C3 at the bottom of the seventh resin tower, and fraction D was recovered through the cock D1 at the bottom of the fifth resin tower.

Further, as a fourth step, the cock R2, a cock E8, a cock C4 and a cock D2 were opened, and the all other cocks were closed. The mixed solution of fraction C and fraction D was introduced into the sixth resin tower through a cock F2-2, while forming a circulation flow in the fifth to eighth resin towers. At the same time, eluent (2) was supplied to the eighth resin tower through the cock E8. Thus, fraction C was recovered through the cock C4 at the bottom of the eighth resin tower, and fraction D was recovered through the cock D2 at the bottom of the sixth resin tower. The first to fourth steps were hereafter repeated to conduct continuous operation. In a cycle having no preparatory step, the mixed solution of fraction C and fraction D was divided into four equal parts Like this, in the second cycle and later, 0.71 liters of the mixed solution of fraction C and fraction D was recovered through each of the cocks F2-1, F2-2, F2-3 and F2-4, 3.49 liters of eluent (2) was supplied through each of the cocks E5, E6, E7 and E8, 0.84 liters of fraction C was recovered through each of the cocks C1, C2, C3 and C4, and 3.36 liters of fraction D was recovered through each of the cocks D3, D4, D1 and D2.

The operating temperature of the second circulation system was 80° C.

In this way, fraction C and fraction D could be separated from each other and recovered by repeating the preparatory step and the first to fourth steps of the second circulation system, in parallel with the respective steps of the first circulation system. Crystallized tyrosine was separated and recovered from the resulting fraction D in the same manner as with Example 1. The recovery of tyrosine was 48%, and the purity thereof was 98%. Powdery neutral amino acids containing leucine and isoleucine as main ingredients and valine, serine and GABA as subsidiary ingredients could be obtained. The recovery of the resulting powdery neutral amino acids from the CR waste liquor was 60% in total. Further, the total content of leucine, isoleucine and valine contained in the powdery neutral amino acids was 53%.

EXAMPLE 8 (Recovering Method 2-2-A; Recovery of GABA)

In the same manner as with Example 6, boiled ion-exchanged water was supplied as an eluent to the third resin layer prepared in Example 5, and fraction numbers 20 to 25 were collected as an amino acid fraction (GABA-rich fraction). The purity of GABA in this GABA-rich fraction was 80%. The above-mentioned GABA-rich fraction was supplied to a fourth resin layer comprising 300 ml of an Mg type IER (DIAION UBK530 manufactured by MITSUBISHI CHEMICAL CORPORATION) at the same solution passage temperature (80° C.), space velocity (0.6 ml/ml·min.) and supply rate (5.56% per resin volume) as a solution allowed to flow out of the first resin layer.

The composition of the GABA-rich fraction allowed to flow out of the fourth resin layer is as shown in FIG. 5 for each fraction number. The effluent of fraction numbers 22 to 28 of FIG. 5 was recovered and concentrated to separate and recover GABA. The recovery of GABA was 30% (based on GABA contained in the raw material), and the purity thereof was 88%.

EXAMPLE 9 (Recovering Method 2-2-A: Recovery of Valine)

In the same manner as with Example 8, boiled ion-exchanged water was supplied as an eluent (80° C.) to the third resin layer prepared in Example 5, and fraction numbers 28 to 30 were collected as an amino acid fraction (valine-rich fraction). The purity of valine in this valine-rich fraction was about 30%. The above-mentioned valine-rich fraction was supplied to the fourth resin layer in the same manner as with Example 9.

The composition of the valine-rich fraction allowed to flow out of the fourth resin layer was as shown in FIG. 6 for each fraction number. The effluent of fraction numbers 19 to 21 of FIG. 6 was recovered and concentrated to separate and recover valine. The recovery of valine was 15% (based on valine contained in the raw material), and the purity thereof was 50%.

EXAMPLE 10 (Recovering Method 3: Recovery of Second Fraction and Recovery of Amino Acids)

In the same manner as with Example 5, the CR waste liquor was fractionated, and the second fraction was supplied to the fourth resin layer comprising 300 ml of the Mg type IER (DIAION UBK530 manufactured by MITSUBISHI CHEMICAL CORPORATION) at the same solution passage temperature, space velocity and supply rate as a solution allowed to flow out of the first resin layer.

Boiled ion-exchanged water was supplied as an eluent (80° C.) to the above-mentioned fourth resin layer. The composition of an effluent allowed to flow out of the fourth resin layer was as shown in FIGS. 7 and 8 for each fraction number. FIG. 7 shows changes in composition of saccharides, amino acids and ashes within the range of fraction numbers 2 to 40 of fraction numbers 1 to 42 collected. Of these, fraction numbers 14 to 31 were collected as an amino acid fraction. FIG. 8 shows changes in composition of the respective amino acids within the range of fraction numbers 14 to 31.

After the amino acid fraction obtained from the fourth resin layer was concentrated to 1/6 by volume, it was adjusted to pH 5.7 with hydrochloric acid. The resulting solution was allowed to stand at room temperature for 24 hours to separate and recover crystallized tyrosine. The recovery of tyrosine was 42% (based on tyrosine contained in the raw material), and the purity thereof was 95%. On the other hand, the separated solution was decolorized with activated carbon, followed by concentration and crystallization to obtain powdery neutral amino acids containing leucine and isoleucine as main ingredients and valine, serine and GABA as subsidiary ingredients. The recovery of the resulting powdery neutral amino acids from the CR waste liquor was 50% (based on the neutral amino acids contained in the raw material). Further, the total content of leucine, isoleucine and valine contained in the powdery neutral amino acids was 36%.

EXAMPLE 11 (Recovering Method 3-2-A; Recovery of GABA)

In the same manner as with Example 10, the CR waste liquor was fractionated, and the second fraction was supplied to the fourth resin layer. Boiled ion-exchanged water was supplied as an eluent (80° C.) to the fourth resin layer, and fraction numbers 22 to 32 were collected as an amino acid fraction (GABA-rich fraction).

The composition of the GABA-rich fraction allowed to flow out of the third resin layer was as shown in FIG. 9 for each fraction number. The effluent of fraction numbers 20 to 27 of FIG. 9 was recovered and concentrated to separate and recover GABA. The recovery of GABA was 31% (based on GABA contained in the raw material), and the purity thereof was 90%.

EXAMPLE 12 (Recovering Method 3-2-A; Recovery of Valine)

In the same manner as with Example 10, the CR waste liquor was fractionated, and the second fraction was supplied to the fourth resin layer. Boiled ion-exchanged water was supplied as an eluent (80° C.) to the fourth resin layer, and fraction numbers 18 to 20 were collected as an amino acid fraction (valine-rich fraction). The purity of valine in this valine-rich fraction was about 30%. The above-mentioned valine-rich fraction was supplied to the fourth resin layer in the same manner as with Example 11. The composition of the valine-rich fraction allowed to flow out of the fourth resin layer was as shown in FIG. 10 for each fraction number. The effluent of fraction numbers 28 to 31 of FIG. 10 was recovered and concentrated to separate and recover valine. The recovery of valine was 25% (based on the neutral amino acids contained in the raw material), and the purity thereof was 50%.

What is claimed is:

1. A method for recovering amino acids, which comprises supplying a mixed solution containing inorganic acid salts, coloring matters, ashes, betaines, amino acids and non-electrolytes including saccharides to a first resin layer comprising a sodium type strongly acidic ion exchange resin or a potassium type strongly acidic ion exchange resin; separating an effluent which flows out of the first resin layer using water or an aqueous solution of caustic alkali as an eluent into at least a first fraction containing coloring matters, acidic amino acids and ashes, a second fraction containing neutral amino acids and saccharides, and a third fraction containing betaines; supplying the second fraction to a second resin layer comprising an ammonium type strongly acidic ion exchange resin to allow the neutral amino acids to be adsorbed by the second resin layer; and recovering an effluent which flows out of the second resin layer using an aqueous solution of ammonia as an eluent, thereby recovering tyrosine and a mixture of the neutral amino acids contained in the effluent.

2. A method for recovering amino acids, which comprises supplying a mixed solution containing inorganic acid salts, coloring matters, ashes, betaines, amino acids and non-electrolytes including saccharides to a first resin layer comprising a sodium type strongly acidic ion exchange resin or a potassium type strongly acidic ion exchange resin; separating an effluent which flows out of the first resin layer using water or an aqueous solution of caustic alkali as an eluent into at least a first fraction containing coloring matters, acidic amino acids and ashes, a second fraction containing amino acids and saccharides, and a third fraction containing betaines; supplying the second fraction to a third resin layer comprising a calcium type strongly acidic ion exchange resin; and separating an effluent which flows out of the third resin layer using water as an eluent into at least a first fraction containing saccharides, amino acids and ashes, and a second fraction containing neutral amino acids including tyrosine, thereby recovering tyrosine and a mixture of the neutral amino acids contained in the effluent.

3. A method for recovering amino acids, which comprises supplying a mixed solution containing inorganic acid salts, coloring matters, ashes, betaines, amino acids and non-electrolytes including saccharides to a first resin layer comprising a sodium type strongly acidic ion exchange resin or a potassium type strongly acidic ion exchange resin; separating an effluent which flows out of the first resin layer using water or an aqueous solution of caustic alkali as an eluent into at least a first fraction containing coloring matters, acidic amino acids and ashes, a second fraction containing amino acids and saccharides, and a third fraction containing betaines, supplying the second fraction to a third resin layer comprising a calcium type strongly acidic ion exchange resin; and separating an effluent which flows out of the third resin layer using water as an eluent into at least a first fraction containing saccharides, amino acids and ashes, a second fraction containing γ-amino butyric acid, alanine and valine, a third fraction containing serine and valine, and a fourth fraction containing leucine, isoleucine and tyrosine, thereby recovering at least one selected from the group consisting of γ-amino butyric acid, alanine, valine, serine, leucine, isoleucine and tyrosine contained in the effluent.

4. The method according to claim 3, wherein neutral amino acids containing γ-amino butyric acid, alanine and valine is recovered from the second fraction of the effluent which flows out of said third resin layer.

5. The method according to claim 3, wherein the second fraction of the effluent which flows out of said third resin layer is further supplied to a fourth resin layer comprising a magnesium type strongly acidic ion exchange resin, and an effluent which flows out of the fourth resin layer using water as an eluent is separated into at least a first fraction containing γ-amino butyric acid and a second fraction containing alanine, valine and serine, thereby recovering γ-amino butyric acid and at least one selected from the group consisting of alanine, valine and serine.

6. The method according to claim 3, wherein neutral amino acids containing serine and valine is recovered from the third fractions of the effluent which flows out of said third resin layer.

7. The method according to claim 3, wherein the third fractions of the effluent which flows out of said third resin layer is further supplied to a fourth resin layer comprising a magnesium type strongly acidic ion exchange resin, and an effluent which flows out of the fourth resin layer using water as an eluent is separated into at least a first fraction containing serine, a second fraction containing valine and a third fraction containing the other neutral amino acids, thereby recovering serine, valine, and the other neutral amino acids.

8. The method according to claim 3, wherein at least one selected from the group consisting of tyrosine, leucine and isoleucine are recovered from the fourth fraction of the effluent which flows out of said third resin layer.

9. A method for recovering amino acids, which comprises supplying a mixed solution containing inorganic acid salts, coloring matters, ashes, betaines, amino acids and non-electrolytes including saccharides to a first resin layer comprising a sodium type strongly acidic ion exchange resin or a potassium type strongly acidic ion exchange resin; separating an effluent which flows out of the first resin layer using water or an aqueous solution of caustic alkali as an eluent into at least a first fraction containing coloring matters, acidic amino acids and ashes, a second fraction containing amino acids and saccharides, and a third fraction containing betaines; supplying the second fraction to a fourth resin layer comprising a magnesium type strongly acidic ion exchange resin; and separating an effluent which flows out of the fourth resin layer using water as an eluent into at least a first fraction containing saccharides, amino acids and ashes, and a second fraction containing neutral amino acids including tyrosine, thereby recovering tyrosine and a mixture of the neutral amino acids contained in the effluent.

10. A method for recovering amino acids, which comprises supplying a mixed solution containing inorganic acid salts, coloring matters, ashes, betaines, amino acids and non-electrolytes including saccharides to a first resin layer comprising a sodium type strongly acidic ion exchange resin or a potassium type strongly acidic ion exchange resin; separating an effluent which flows out of the first resin layer using water or an aqueous solution of caustic alkali as an eluent into at least a first fraction containing coloring matters, acidic amino acids and ashes, a second fraction containing amino acids and saccharides, and a third fraction containing betaines, supplying the second fraction to a fourth resin layer comprising a magnesium type strongly acidic ion exchange resin; and separating an effluent which flows out of the fourth resin layer using water as an eluent into at least a first fraction containing saccharides, amino acids and ashes, a second fraction containing serine, a third fraction containing alanine and valine, and a fourth fraction containing tyrosine, leucine, isoleucine and γ-amino butyric acid, thereby recovering at least one selected from the group consisting of serine, alanine, valine, tyrosine, leucine, isoleucine and γ-amino butyric acid contained in the effluent.

11. The method according to claim 10, wherein neutral amino acids containing alanine and valine is recovered from the third fraction of the effluent which flows out of said fourth resin layer.

12. The method according to claim 10, wherein the third fraction of the effluent which flows out of said fourth resin layer is further supplied to a third resin layer comprising a calcium type strongly acidic ion exchange resin, and an effluent which flows out of the third resin layer using water as an eluent is separated into at least a first fraction containing alanine, a second fraction containing valine, and a third fraction containing the other neutral amino acids, thereby recovering alanine, valine and the other neutral amino acids.

13. The method according to claim 10, wherein the fourth fraction of the effluent which flows out of said fourth resin layer is further supplied to a third resin layer comprising a calcium type strongly acidic ion exchange resin, and an effluent which flows out of the third resin layer using water as an eluent is separated into at least a first fraction containing γ-amino butyric acid, and a second fraction containing tyrosine, leucine and isoleucine, thereby recovering γ-amino butyric acid and at least one selected from the group consisting of tyrosine, leucine and isoleucine.

14. The method according to any one of claims 1 to 13, wherein an aqueous solution of caustic alkali having a pH of 8.5 to 11.0 is used as the eluent for said first resin layer.

* * * * *